United States Patent [19]
Cawse

[11] 3,948,965
[45] Apr. 6, 1976

[54] CATALYTIC PROCESS FOR POLYHYDRIC ALCOHOLS AND DERIVATIVES
[75] Inventor: James N. Cawse, Charleston, W. Va.
[73] Assignee: Union Carbide Corporation, New York, N.Y.
[22] Filed: July 12, 1974
[21] Appl. No.: 488,603

[52] U.S. Cl. ..... 260/449 R; 252/431 R; 252/431 N; 252/431 L; 252/431 P; 252/443; 260/449 L; 260/485 G; 260/488 J; 260/449.5
[51] Int. Cl.² ..... C07C 27/06
[58] Field of Search ......... 260/449 R, 449 L, 449.5; 252/431 R, 431 N, 431 L, 431 P, 443

[56] References Cited
UNITED STATES PATENTS

| | | | |
|---|---|---|---|
| 3,081,357 | 3/1963 | Alderson et al. | 252/443 |
| 3,487,112 | 12/1969 | Paulik et al. | 252/431 P |
| 3,560,539 | 2/1971 | Booth | 252/431 P |
| 3,641,076 | 2/1972 | Booth | 252/431 P |
| 3,833,634 | 9/1974 | Pruett et al. | 260/449 R |

FOREIGN PATENTS OR APPLICATIONS

| | | | |
|---|---|---|---|
| 793,086 | 6/1973 | Belgium | 260/449 |

OTHER PUBLICATIONS

Martinengo et al., Gazz, 102 (1972), pp. 344–354.

Primary Examiner—Howard T. Mars
Attorney, Agent, or Firm—George A. Skoler

[57] ABSTRACT

This invention relates to the manufacture of such valuable chemicals as polyhydric alcohols, their ether and ester derivatives, oligomers of such alcohols and monohydric alcohols and their ether and ester derivatives by reacting oxides of carbon and hydrogen in the presence of a bis(triorgano phosphine)iminium cation and a rhodium carbonyl complex provided to the reaction as a rhodium carbonyl cluster anion which possesses an infrared spectrum which exhibits three intense wavelength bands between about plus and minus 10 $cm^{-1}$ of about 1868 $cm^{-1}$, about 1838 $cm^{-1}$, and about 1785 $cm^{-1}$ at a pressure of at least about 500 pounds per square inch absolute.

18 Claims, No Drawings

CATALYTIC PROCESS FOR POLYHYDRIC ALCOHOLS AND DERIVATIVES

This invention is concerned with a process for the manufacture of polyhydric alcohols, their ether and ester derivatives, and oligomers of such alcohols. This invention also produces monohydric alcohols such as methanol, and their ether and ester derivatives.

Polyhydric alcohols are presently being produced synthetically by the oxidation of petroleum derived materials. Owing to the limited availability of petroleum sources, the cost of these petroleum derived materials has been steadily increasing. Many have raised the dire prediction of a significant oil shortage in the future. The consequence of this has been the recognition of the need for a new low cost source of chemicals which can be converted into such polyhydric alcohols.

It is known that monofunctional compounds such as methanol can be obtained by reaction between carbon monoxide and hydrogen at elevated pressures e.g., up to about 1000 atmospheres, and temperatures ranging from 250°C to 500°C, using mixtures of copper, chrominum and zinc oxides as the catalyst therefor. It is disclosed in U.S. Pat. No. 2,451,333 that polyhydroxyl compounds are produced by reaction of formaldehyde, carbon monoxide, and hydrogen in the presence of hydrogenation catalysts. It has also been reported that formaldehyde can be produced by reaction between carbon monoxide and hydrogen at elevated pressures but repeated attempts to carry out this synthesis of formaldehyde have invariably failed to yield any substantial quantity of the desired product. It is generally recognized that the previously disclosed processes for the synthesis of formaldehyde from carbon monoxide and hydrogen at high pressures are either completely inoperative or else give rise to insignificantly small quantities of formaldehyde.

In British Pat. No. 655,237, published July 11, 1951, there is disclosed the reaction between carbon monoxide and hydrogen at elevated pressures and temperatures up to 400°C, using certain hydrogenation catalysts as exemplified by cobalt-containing compounds. U.S. Pat. Nos. 2,534,018; 2,570,792 and 2,636,046 are substantially similar in disclosure to the above said British patent. The only catalysts employed in the numbered examples of said U.S. Pat. 2,636,046 are those which contain cobalt.

It is also well-known that nickel is predominantly a catalyst for synthesis and for reforming methane according to the reaction

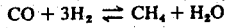

which proceeds from left to right at temperatures below about 500°C. and in the opposite direction at higher temperatures; see Kirk-Othmer, Encyclopedia of Chemical Technology, Second Edition, Volume 4, pages 452–453, John Wiley and Sons, New York (1964).

In copending application Ser. No. 219,130, filed Jan. 19, 1972 now U.S. Pat. No. 3,833,634, and Belgium Pat. No. 793,086, published June 20, 1973, there is disclosed a process for the preparation of polyhydric alcohols by contacting a mixture of carbon monoxide and hydrogen with a catalytic amount of rhodium in complex combination with carbon monoxide.

Copending application, Ser. No. 462,109, filed Apr. 19, 1974, characterizes an improvement on the invention of Ser. No. 219,130. There is disclosed in Ser. No. 462,109 a process for manufacturing polyhydric alcohols, their ether and ester derivatives, oligomers of such alcohols and monohydric alcohols and their ether and ester derivatives by reacting the oxides of carbon and hydrogen in the presence of a rhodium carbonyl complex which is provided to the reaction as a rhodium carbonyl cluster which possesses an infrared spectrum which exhibits three intense wavelength bands between about plus and minus 10 cm$^{-1}$ of about 1868 cm$^{-1}$, about 1838 cm$^{-1}$, and about 1785 cm$^{-1}$ at a pressure of at least about 500 pounds per square inch, in association with a counter-ion. Suitable counter-ions for the cluster are a variety of metals and organic compounds.

This invention is directed to a process for making polyhydric aliphatic alcohols and their ether, ester, and oligomer derivatives, such as alkane polyols, most specifically, alkane diols and triols, containing 2 or 3 carbon atoms, their ether, ester and oligomer derivates.

As with the process of Serial No. 462,109, a byproduct of this invention is the manufacture of the lesser valuable, but valuable nevertheless, monohydric alkanols such as methanol, ethanol, and propanol, and their ether and ester derivatives. The products of this invention contain carbon, hydrogen and oxygen.

The present invention is concerned with an improved and more stable catalyst system which enhances the production of polyhydric alcohols, their ether and ester derivatives, oligomers of such alcohols, monohydric alcohols and their ether and ester derivatives at lower catalyst concentrations, contact times, and operating temperatures and pressures. The improved catalyst system of the present invention involves reacting the oxides of carbon and hydrogen in the presence of a bis(triorgano phosphine)iminium cation and a rhodium carbonyl complex which is provided to the reaction as a rhodium carbonyl cluster which possesses an infrared spectrum which exhibits three intense wavelength bands between about plus and minus 10 cm$^{-1}$ of about 1868 cm$^{-1}$ about 1838 cm$^{-1}$ and 1785 cm$^{-1}$ at a pressure of at least about 500 pounds per square inch absolute.

The rhodium carbonyl cluster of this invention exhibits the above infrared spectrum either during the reaction or at a temperature and/or pressure below that at which the reaction is effected. In both instances, the catalytic effect is achieved suggesting that the characterized rhodium clusters are always present.

Suitable bis(triorgano phosphine)iminium cations useful in the present invention include those of the formula:

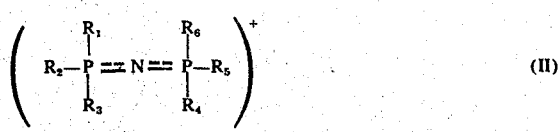

wherein R$_1$, R$_2$, R$_3$, R$_4$, R$_5$ and R$_6$ are any organic radicals which do not adversely affect the production of polyhydric alcohols by reacting oxides of carbon and hydrogen in the presence of the aforedefined rhodium carbonyl cluster, such as a straight or branched chain alkyl group, having from 1 to 20 carbon atoms in the alkyl chain, such as methyl, ethyl, n-propyl, isopropyl, n-butyl, octyl, 2-ethyl hexyl, dodecyl, and the like; or a cycloaliphatic group, that is cycloalkyl including the monocyclic and bicyclic groups cyclopentyl, cyclohexyl, and bicyclo-[2.2.1] heptyl groups, and the like; or an aryl, alkylaryl, or araalkyl group such as phenyl, naphthyl, xylyl, tolyl, t-butylphenyl, benzyl, beta-phenylethyl, 3-phenylpropyl and the like; or a functionally substituted alkyl such as beta-hydroxyethyl, ethoxymethyl, ethoxyethyl, phenoxyethyl and the like; or a polyalkylene ether group of the formula — $C_nH_{2n}O)_x$-OR wherein $n$ has an average value from 1 to 4, $x$ has an average value from 2 to about 150, and R may be hydrogen or alkyl of 1 to about 12 carbon atoms. Illustrative of such polyalkylene ether groups are poly(oxyethylene), poly(oxypropylene), poly(oxyethyleneoxypropylene), poly(oxyethyleneoxybutylene), and the like.

P. Chini, in a review article entitled "The Closed Metal Carbonyl Clusters" published in Review (1968), Inorganica Chemica Acta, pages 30–50, states that a metal cluster compound is "a finite group of metal atoms which are held together entirely, mainly, or at least to a significant extent, by bonds directly between the metal atoms even though some non-metal atoms may be associated intimately with the cluster". The rhodium carbonyl cluster compounds of this invention contain rhodium bonded to rhodium or rhodium bonded to another metal, such as cobalt, and/or iridium. The preferred rhodium carbonyl cluster compounds of this invention are those which contain rhodium-rhodium bonds. These compounds desirably contain carbon and oxygen in the form of carbonyl (—C-O), in which the carbonyl may be "terminal", "edge bridging", and/or "face bridging". They may also contain hydrogen and carbon in forms other than carbonyl. The following are illustrative of what is believed to be the structure of two distinct rhodium carbonyl cluster ions and both are suitable for use in this invention:

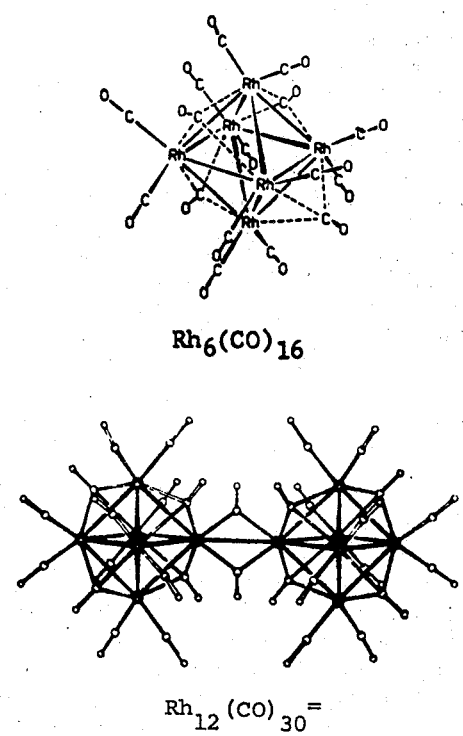

$Rh_6(CO)_{16}$ $Rh_{12}(CO)_{30}^=$

The structures of the rhodium carbonyl clusters may be ascertained by X-ray crystal diffraction, nuclear magnetic resonance, spectra, NMR, or infrared spectra as disclosed in the article entitled "Synthesis and Properties of the Derivatives of the $[Rh_{12}(CO)_{30}]^{2-}$ Anion" by P. Chini and S. Martinengo; appearing in Inorganica Chemica Acta, 3:2 pp299-302, June (1969). Of particular analytical utility in the present invention is the use of infrared spectroscopy which allows for qualitative and what is presently believed to be a quantitative characterization of the particular rhodium carbonyl cluster present during the operation of the process of the present invention.

Rhodium carbonyl cluster ions which possess the infrared spectrum characterized previously, function in association with oxides of carbon and hydrogen, as herein defined, to produce the polyhydric alcohols, etc. The exact mechanism by which the cluster compounds act to catalyze the reaction is not fully appreciated at this time. It is believed that the reaction is dependent upon the existence of the following equilibria:

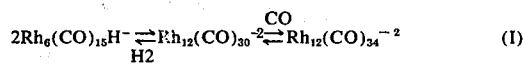

(I)

Such an equilibria may be in situ formed from a less complex rhodium carbonyl compound or a more complexed rhodium carbonyl compound. However, it may be that such cluster equilibria is symptomatic of an intermediate transitory rhodium carbonyl structure which serves to radicalize two molecules of carbon monoxide which are subsequently converted to the polyhydric alcohol.

The precise role of the bis(triorgano phosphine)iminium cation in the reaction of carbon monoxide and hydrogen catalyzed by the rhodium carbonyl clusters to produce polyhydric alcohols is not clearly understood. The reaction is believed to involve the reaction of carbon monoxide with the active catalytic species to form a radical of CO which may or may not require the addition of another radical of CO prior to hydrogenation to form the polyhydric alcohol or methanol. Infrared analysis shows that under reaction conditions which favor the production of polyhydric alcohols, the characteristic 3 band pattern of the $[Rh_{12}(CO)_{34}]^{2-}$ cluster is present; while under conditions which favor the production of methanol, only the single band pattern, about 1900 cm$^{-1}$, of the monomeric $Rh(CO)_4^-$ anion is dominant and the aforementioned 3 band pattern is missing or minimized in intensity. In terms of the results achieved, it would appear that the bis(triorgano phosphine)iminium cation functions in a manner which may reduce factors which inhibit the aforementioned CO radical formation.

The rhodium carbonyl complex is, as characterized above, a rhodium containing compound in which the rhodium values are complexed with CO. This can be achieved with just CO, hydrogen and the bis(triorgano phosphine)iminium cation, or there may be included other organic materials to create the complex. In the last case, "complex" means a coordination compound formed by the union of one or more electronically rich organic molecules or atoms capable of independent existence with one or more electronically poor molecules or atoms, each of which is also capable of independent existence. These organic rhodium cluster complexes are derived from the association of organic ligands or organic counter-ions with rhodium carbonyl solutions.

Organic ligands which are suitable in the practice of the invention contain at least one nitrogen atom (hereinafter called Lewis base nitrogen atom) and/or at least one oxygen atom (hereinafter called Lewis base oxygen atom), said atoms possessing a pair of electrons available for the formation of coordinate bonds with rhodium. Suitably the organic ligand contains at least two Lewis base nitrogen atoms, or at least two Lewis base oxygen atoms, or at least one Lewis base nitrogen atom plus at least one Lewis base oxygen atom, said atoms possessing a pair of electrons available for the formation of coordinate bonds with rhodium, and said organic ligand forming with rhodium per se a chelate structure. In suitable embodiments the organic ligands contain from 1 and upwards to 4 Lewis base atoms, preferably from 1 to 30 such atoms, and most preferably 1 or 2 Lewis base atoms. These organic ligands are said to be multidentate or polydentate, that is to say, such ligands are bidentate, tridentate, or quadridentate, depending on whether 2, 3, or 4 Lewis base atoms are involved in the formation of chelate structures with rhodium.

Organic ligands which contain at least one Lewis base nitrogen atom will oftentimes hereinafter be referred to as "organic nitrogen ligands"; those ligands which contain at least one Lewis base oxygen atom will oftentimes be referred to as "organic oxygen ligands"; and those which contain at least one Lewis base nitrogen atom plus at least one Lewis base oxygen atom will oftentimes be referred to as "organic aza-oxa ligands".

Suitable organic nitrogen ligands most generally contain carbon, hydrogen, and nitrogen atoms. Suitable organic oxygen ligands most generally contain carbon, hydrogen, and oxygen atoms. Suitable organic aza-oxa ligands most generally contain carbon, hydrogen, oxygen, and nitrogen atoms. The carbon atoms can be acyclic and/or cyclic such as aliphatic cycloaliphatic, aromatic (including fused and bridged) carbon atoms, and the like. Preferably, the organic ligands contain from 2 to 20 carbon atoms. The nitrogen atoms can be in the form of imino (—N=), amino (—N—), nitrilo (N ≡ ), etc. Desirably, the Lewis base nitrogen atoms are in the form of imino nitrogen and/or amino nitrogen. The oxygen atoms can be in the form of groups such as hydroxyl (aliphatic or phenolic), carboxyl

, carbonyloxy

, oxy (—O—), carbonyl

, etc., all of said groups containing Lewis base oxygen atoms. In this respect, it is the "hydroxyl" oxygen in the

group and the "oxy" oxygen in the

group that are the Lewis base atoms. The organic ligands may also contain other atoms and/or groups such as alkyl, cycloalkyl, aryl, chloro, thiaalkyl, trialkylsilyl, and the like.

Illustrative organic nitrogen ligands include for instance, N,N,N',N'-tetramethylethylenediamine, N,N,N',N'-tetraethylethylenediamine, N,N,N',N'-tetra-n-propylethylenediamine, N,N,N',N'-tetramethylmethylenediamine, N,N,N',N'-tetraethylmethylenediamine, N,N,N',N'-tetraisobutylmethylenediamine, piperazine, N-methylpiperazine, N-ethylpiperazine, 2-methyl-N-methylpiperazine, 2,2'-dipyridyl, methyl-substituted 2,2'-dipyridyl, ethyl-substituted 2,2'-dipyridyl, 1,4-diazabicyclo [2.2.2] octane, methyl-substituted 1,4-diazabicyclo [2.2.2] octane, purine, 2-amino-pyridine, 2-(dimethylamino) pyridine, 1,10-phenan-throline, methyl-substituted 1,10-phenanthroline, 2-(dimethylamino)-6-methoxyquinoline, 7-chloro-1,10-phenanthroline, 4-triethylsilyl-2,2'-dipyridyl, 5-(thiapentyl)-1,10-phenanthroline, and the like.

Illustrative organic oxygen ligands include, by way of illustrations, glycolic acid, methoxyacetic acid, ethoxyacetic acid, digylcolic acid, thiodiglycolic acid, diethyl ether, tetrahydrofuran, dioxane, tetrahydropyran, pyrocatechol, citric acid, 2-methoxy-ethanol, 2-ethoxyethanol, 2-n-propoxyethanol, 2-n-butylethanol, 1,2,3-trihydroxybenzene, 1,2,4-trihydroxybenzene, 2,3-dihydroxynaphthalene, cyclohexane-1,2-diol, oxetane, 1,2-dimethoxybenezene, 1,2-diethoxybenzene, methyl acetate, ethanol, 1,2-dimethoxyethane, 1,2-diethoxyethane, 1,2-di-n-propoxyethane. 1,2-di-n-butoxyethane, pentane-2,4-dione, hexane-2,4-dione, heptane-3,5-dione, octane-2,4-dione, 1-phenylbutane-1,3-dione, 3-methylpentane-2,4-dione; the mono- and dialkyl ethers of propylene glycol, of diethylene glycol, of dipropylene glycol; and the like.

Illustrative organic aza-oxa ligands include, for example, ethanolamine, diethanolamine, isopropanolamine, di-n-propanolamine, N,N-dimethylglycine, N,N-diethylglycine, iminodiacetic acid, N-methyliminodiacetic acid, N-methyldiethanolamine, 2-hydroxypyridine, methyl-substituted 2-hydroxypyridine, picolinic acid, methyl-substituted picolinic acid, nitrilotriacetic acid, 2,5-dicarboxypiperazine, N-(2-hydroxyethyl) iminodiacetic acid, ethylenediaminetetraacetic acid, 2,6-dicarboxypyridine, 8-hydroxyquinoline, 2-carboxyquinoline, cyclohexane-1,2-diamine-N,N,N',N'-tetraacetic acid, the tetramethyl ester of ethylenediaminetetraacetic acid, and the like.

Illustrative of other Lewis base nitrogen containing compounds suitable for use in the practice of the present invention are, e.g., piperidine, 2-methylpiperidine, 3-methylpiperidine, pyridine, 2-methylpyridine, 4-ethylpiperidine, triethylamine, benzyltrimethyl ammonium acetate and formate, tri-n-butylamine, dibutylamine, methylamine, dodecylamine, morpholine, aniline, benzylamine, octadecylamine, naphthylamine, cyclohexylamine, and the like. The precise role of these compounds in the practice of the present invention is not fully understood at present. It is believed that they may be acting as ligands and/or forming counter-ions, which ionically associate with the rhodium carbonyl cluster ions, under reaction conditions of the present process.

In the practice of the present invention a normally liquid organic solvent is employed in an amount sufficient to maintain a homogeneous reaction mixture containing the cluster and the bis (triorgano phosphine) iminium cation. Illustrative of the solvents which are generally suitable in the practice of the present invention include, for example, saturated and aromatic hydrocarbons, e.g., hexane, octane, dodecane, naphtha, decalin, tetrahydronaphthalene, kerosene, mineral oil, cyclohexane, cycloheptane, alkylcycloalkane, benzene, toluene, xylene, naphthalene, alkylnaphthalene, etc.; ethers such as tetrahydrofurna, tetrahydropyran, diethyl ether, 1,2-dimethoxybenzene, 1,2-ethoxybenzene, the mono-and dialkyl ehters of alkylene glycols and polyalkylene glycols, such as ethylene glycol, of propylene glycol, of butylene glycol, of diethylene glycol, of dipropylene glycol, of triethylene glycol, of tetraethylene glycol, of pentaethylene glycol, of dibutylene glycol, of oxyethyleneoxypropylene glycol, etc., preferably, those in which the alkylene group contains 2 carbon atoms in the divalent moiety, such as, ethylene and 1,2-propylene; carboxylic acids such as acetic acid, propionic acid, butyric acid, caproic acid, stearic acid, benzoic acid, cyclohexanecarboxylic acid, etc.; alkanols such as methanol, ethanol, propanol, isobutanol, 2-ethylhexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; water; anhydrides such as phthalic anhydride, acetic anhydride, etc.; lactones such as γ-butyrolactone and δ-valerolactone, etc.; and others γ-butyrolactone and the mono and dialkylethers of triethylene and tetraethylene glycol are the preferred solvents in the practice of the present invention.

It should be noted that the use of reactive solvents in the practice of desirable embodiments of the invention can give rise to a range of useful products. For instance, the mono- and diacetate esters of ethylene glycol can be obtained by using acetic acid as the solvent in the reaction medium. The use of alkanols, e.g., methanol and ethanol, can result in the monoalkyl ethers of ethylene glycol.

In one of the embodiments of the present invention the bis(triorgano phosphine) iminium cation is provided to the reaction mixture in its simple salt form. Suitable salts useful in the present invention include those of the general formula R'X wherein R' may be any of the bis(triorgano phosphine) iminium cations defined by formula (I) above and X may be hydroxide; a halogen, such as fluorine, chlorine, bromine and iodine; a carboxylate group, such as formate, acetate, propionate and butyrate and the like; an alkoxide group such as methoxide, ethoxide, phenoxide, and the like; a functionally substituted alkoxide or phenoxide group such as methoxyethoxide, ethoxyethoxide, phenoxyethoxide and the like; a pyridinolate or quinolinolate group; and others. These bis(triorgano phosphine)iminium salts may be prepared by carrying out the following reactions in a suitable solvent such as 1,1,2,2-tetrachloroethane;

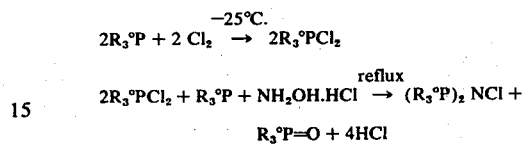

wherein R° may have any of the values of $R_{1-6}$ in formula (II). The $(R°_3P)_2NCl$ can be crystallized from ethyl acetate usually upon standing overnight and then recrystallized from boiling water.

Another suitable method for preparing the $(R°_3P)_2N^+$ salts is disclosed in an article by Appel, R. and Hanas, A. appearing in Z. Anorg. u. Allg. Chem., 311, 290, (1961).

In another embodiment of the present invention, the anion of the bis(triorgano phosphine) iminium salt may be one of the anionic rhodium carbonyls which are capable of yielding the $[Rh_{12}(CO)_{34}]^{2-}$ cluster under the reaction conditions of the present process. Suitable rhodium carbonyl anions include $[Rh_6(CO)_{15}]^{2-}$, $[Rh_6(CO)_{15}Y]^-$ wherein $\underline{Y}$ may be halogen, such as chlorine, bromine or iodine, $[Rh_6(CO)_{15}(COOR'')]^-$ wherein R'' is lower alkyl or aryl such as methyl, ethyl or phenyl, $[Rh_6(CO)_{14}]^{2-}$, $[Rh_7(CO)_{16}]^{3-}$, and $[Rh_{12}(CO)_{30}]^{2-}$.

The bis(triorgano phosphine)iminium rhodium carbonyl cluster salts may be prepared by dissolving the alkali metal or tetraalkylammonium salts of the rhodium carbonyl cluster in a suitable solvent such as tetrahydrofuran (THF) and then adding the desired bis(triorgano phosphine)iminium acetate salt, slightly in excess of the stoichiometric amount. The mixture is stirred at room temperature from about 2 to about 30 minutes and/or until solution is effected as evidenced by the particular clusters' coloration of the solution (brownish for $Rh_6$ cluster anions, greenish for $Rh_7$ cluster anions, and purpluish for $Rh_{12}$ cluster anions), and then water is added in a sufficient amount (from about 50 to about 200 percent by weight of the solvent) to crystallize out the bis(triorgano phosphine) iminium rhodium carbonyl cluster salt. In preparing the $[Rh_7(CO)_{16}]^{3-}$ salt acetonitrile is the preferred solvent.

In preparing the $(R°_3P)_2N_-$ salts of the $Rh_6$ and $Rh_7$ carbonyl clusters it is preferred to carry out the reaction in the absence of water. A suitable method would be to add the chloride salt of $(R°_3P)_2N^+$ to the solution of the alkali metal cluster salt whereby the alkali metal chloride precipitates out leaving the $(R°_3P)_2N^+$ cluster salt behind in solution. The $(R°_3P)_2N^+$ cluster salt can be recovered by filtering off the insoluble alkali metal chloride and low temperature, low pressure evaporation of the filtrate solution.

The above alkali metal and tetralkyl ammonium rhodium carbonyl cluster salts may be prepared by the methods disclosed in the following articles by P. Chini and S. Martinengo.

"Synthesis and Characterisation of the $[Rh_6(CO)_{15}]^{2-}$ and $[Rh_7(CO)_{16}]^{3-}$ Anions", P. Gazetta Chimica Italiana, 102, pp 344–354, (1972), and "Synthesis and Properties of the Derivatives of the $[Rh_{12}(CO)_{30}]^{2-}$ Anion", Inorganica Chemica Acta, 3:2, pp 299–302, (June 1969).

The quantity of bis(triorgano phosphine) iminium cation that is provided to the reaction can vary over wide limits. Preferably the cation is present in the reaction mixture in an amount of about 0.8 to about 2.0 moles of the iminium cation for every 6 moles of rhodium present in the reaction mixture. More preferably the iminium cation is present in the reaction mixture in an amount of about 1.2 to about 1.6 moles, most preferably about 1.2 to about 1.4 moles, for every six moles of rhodium present in the reaction mixture.

The quantity of catalyst employed is not narrowly critical and can vary over a wide range. In general, the novel process is desirably conducted in the presence of a catalytically effective quantity of the active rhodium species which gives a suitable and reasonable reaction rate. Reaction proceeds when employing as little as about $1 \times 10^{-6}$ weight percent, and even lesser amounts, of rhodium metal based on the total weight of reaction mixture. The upper concentration limit can be quite high, e.g., about thirty weight percent rhodium, and higher, and realistic upper limit in practicing the invention appears to be dictated and controlled more by economics in view of the exceedingly high cost of rhodium metal and rhodium compounds. No particular advantages at the relatively high concentrations of rhodium are manifest. Depending on various factors such as the cation of choice, the partial pressures of oxides of carbon and hydrogen, the total operative pressure of the system, the operative temperature, the choice of the normally-liquid organic solvent, and other considerations, a catalyst concentration of from about $1 \times 10^{-5}$ to about $1 \times 10^{-1}$ weight percent rhodium (contained in the complex catalyst) based on the total weight of reaction mixture, is generally desirable in the practice of the invention.

The operative temperature which may be employed can vary over a wide range of elevated temperatures. In general, the novel process can be conducted at a temperature in the range of from about 100°C. and upwards to approximately 375°C., and higher. Operative temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, signs of some catalyst instability are noted. Notwithstanding this factor, reaction continues and polyhydric alcohols and/or their derivatives are produced. Suitable operative temperatures are between about 150°C. to about 300°C., preferably from about 190°C. to about 275°C., and more preferably about 190°C. to about 240°C.

The equilibrium reaction for forming ethylene glycol is:

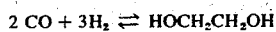

At relatively high temperatures the equilibrium increasingly favors the left hand side of the equation. In practice of the present invention, to drive the reaction to the formation of a fixed increased quantity of ethylene glycol, lower partial pressures of carbon monoxide and hydrogen are required than those taught by the prior art.

This novel process is suitably effected over a wide superatmospheric pressure range. At pressures below about 500 psia, the rate of desired product formation is quite slow, and consequently, relatively faster reaction rates and/or higher conversions to the desired product can be obtained by higher operative pressures, e.g., at a pressure of at least about 800 psia. Pressures as high as 50,000 psia, and higher, can be employed but with no apparent advantages attendant thereto which offset the unattractive plant investment outlay required for such high pressure equipment. However, at pressures greater than about 15,000 psia no improvement in the productivity of polyhydric alcohol can be attributed to the presence of the bis(triorgano phosphine) iminium cation in the select amount. This non-beneficial effect of the cation at high pressures is believed due to the overriding effect the increased pressure of carbon monoxide has on the stability of the rhodium carbonyl cluster. A suitable pressure range for effecting the novel process is from about 1000 psia to about 15,000 psia, preferably about 2000 psia to about 12,000 psia, and more preferably about 6,000 psia to about 10,000 psia. The pressures referred to above represent the total pressure of hydrogen and oxides of carbon.

The novel process is effected for a period of time sufficient to produce the desired polyfunctional oxygen-containing products and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressure exerted by its components, the concentration and choice of diluent, and other factors. The synthesis of the desired product(s) by the reaction of hydrogen with an oxide of carbon is suitably conducted under operative conditions which give reasonable reaction rates and/or conversions.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5. It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semicontinuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "run-away" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with-/without make-up carbon monoxide and hydrogen to the reactor. Recovery of the desired product can be achieved by methods well-known in the art such as by distillation, fractionation, extraction, and the like. A fraction comprising rhodium catalyst, generally contained in byproducts and/or normally liquid organic diluent, can be recycled to the reaction zone, if desired. All or a portion of such fraction can be removed for recovery of the rhodium values or regeneration to the active rhodium species, if necessary. Fresh rhodium catalyst can be intermittently added to the recycle stream or directly to the reaction zone.

The active forms of the rhodium carbonyl clusters may be prepared by various techniques. They can be preformed as indicated previously and then introduced into the reaction zone. Alternatively, any of the host of rhodium-containing substances as well as the cation forming substances can be introduced into the reaction zone and, under the operative conditions of the process (which of course includes hydrogen and carbon monoxide), the active rhodium carbonyl cluster can be generated in situ. Illustrative of rhodium-containing substances which can be conveniently introduced or placed in the synthesis zone include, for example, rhodium oxide, $(Rh_2O_3)$, tetrarhodium dodecacarbonyl, dirhodium octacarbonyl, hexarhodium hexadecarbonyl $(Rh_6(CO)_{16})$, rhodium (II) formate, rhodium (II) acetate, rhodium (II) propionate, rhodium (II) butyrate, rhodium (II) valerate, rhodium (III) naphthenate, rhodium dicarbonyl acetylacetonate, rhodium tris(acetylacetonate), rhodium trihydroxide, indenylrhodium dicarbonyl, rhodium dicarbonyl (1-phenylbutane-1,3-dione), tris (hexane-2,4-dionato)rhodium (III), tris(-heptane-2,4-dionato)rhodium(III), tris (1-phenylbutane-1,3-dionato)rhodium(III), tris(3-methylpentane-2,4-dianato(rhodium(III) and tris(1-cyclohexylbutane-1,3-dionato(rhodium(III).

The preparation of rhodium carbonyl cluster compounds is conveniently carried out in a diluent or mixture of diluents, e.g., benzene. Tetrarhodium dodecarbonyl, though of limited solubility, can be added to the diluent in a finely divided form. Any of several of the rhodium-containing compounds illustrated previously can be employed in lieu of $Rh_4(CO)_{12}$. Organic ligands such as 2-hydroxypyridine or other counter-ion forming compounds can also be added thereto. The cluster forming reaction can be effected under a carbon monoxide pressure, with or without $H_2$, of about 1 to about 15 atmospheres, and higher, using a temperature of about 30°C. to about 100°C., for a period of time ranging from minutes to a few days, generally from about 30 minutes to about 24 hours. The resulting rhodium cluster compound contained in the organic diluent is catalytically active in this process. The compound contains rhodium in clustered combination with carbon monoxide and the counter ion of choice.

The equipment arrangement and procedure which provides the capability for determining the existence of rhodium carbonyl clusters having the aforedefined infrared spectrum characteristics, during the course of the manufacture of polyhydric alcohols from carbon monoxide and hydrogen, pursuant to this invention, is disclosed and schematically depicted in U.S. Pat. application, Ser. No. 462,109, filed Apr. 18, 1974, the disclosure of which is incorporated herein by reference.

A particularly desirable infrared cell construction is described in copending U.S. Pat. application, Ser. No. 451,437, filed Mar. 15, 1974, and its disclosure of a preferred cell construction is incorporated herein by reference.

The "oxide of carbon" as covered by the claims and as used herein is intended to mean carbon monoxide and mixtures of carbon dioxide and carbon monoxide, either introduced as such or formed in the reaction.

The following examples are merely illustrative and are not presented as a definition of the limits of the invention.

EXAMPLE 1

A 150 ml. capacity stainless steel reactor capable of withstanding pressures up to 7,000 atmospheres was charged with a premix of 75 cubic centimeters (cc) of the dimethylether of tetraethylene glycol (tetraglyme), 3.0 millimoles (mm) .77 gms, of rhodium dicarbonylacetylacetonate $(Rh(CO)_2AcAc)$, 10 millimoles (mmol) of distilled 2-hydroxypyridine. The reactor was sealed and charged with a gaseous mixture, containing equal molar amounts of carbon monoxide and hydrogen, to a pressure of 8,000 pounds per square inch (psig). Heat was applied to the reactor and its contents, when the temperature of the mixture inside the reactor reached 190°C., as measured by a suitably placed thermocouple, and additional adjustment of carbon monoxide and hydrogen ($H_2$:CO=1:1 mole ratio) was made to bring the pressure back to 8000 psig. The temperature was maintained at 220° C. for 4 hours. During this period of time additional carbon monoxide and hydrogen was added whenever the pressure inside the reactor dropped below about 7500 psig. With these added repressurizations the pressure inside the reactor was maintained at 8000 psig ± 400 psig over the entire 4 hours period.

After the 4 hour period, the vessel and its contents were cooled to room temperature, the excess gas vented and the reaction product mixture was removed. Analysis of the reaction product mixture was made by gas chromatographic analysis using a Hewlitt Packard FM™ 101. The gas chromatograph is held at 50° for minutes after introduction of two microliters of product sample and then programmed from 50° to 280°C. at 15°C. per minute.

Analysis of the product mixture shows 2.1 grams of methanol, 1.0 grams of ethylene glycol, 0.15 grams of methyl formate, 0.02 grams of ethanol, 0.03 grams of ethyleneglycol monoformate and the rhodium recovered was 75 percent based on the total rhodium charged to the reactor.

The amount of rhodium recovered from the reactor is determined by atomic absorption analysis of the reaction mixture after the four hours of reaction time had lapsed and the unreacted gases were vented to the atmosphere. Atomic absorption analysis was run using a Perkin and Elmer Model 303 Atomic Absorption Spectrophotometer, sold by Perkin and Elmer of Norwalk, Conn. Rhodium recovered therefore would be the percent of the total rhodium charged that is still soluble or suspended in the reaction mixture at the end of the four hour reaction time.

The bis(triphenyl phosphine) iminium acetate used in Example 2 and all of the following examples was crystallized from ethanol in its ethanol solvate form. The crystallized salt upon analysis showed it to contain one mole of ethanol for every mole of bis(triphenyl phosphine) iminium acetate.

The same equipment and procedure used in Example 1 were used in Examples 2 through 39 except for the reactants and conditions specified. The bis(triphenyl phosphine)iminium acetate ethanol solvate salt was added with the initial charge of reactants in Examples 2 through 39.

TABLE I[1]

| Example | $(PH_3P)_2N^+$, mmol.[2] | Solvent | Methanol | Ethylene Glycol | Methyl Formate | Products, grams Glycol Monoformate | Glycerine | Propylene Glycol | Rhodium Recovery |
|---|---|---|---|---|---|---|---|---|---|
| 2 | .25 | Tetraglyme[3] | 1.9 | 2.0 | N.D[5] | 0.6 | N.D | N.D | 77 |
| 3 | .5 | " | 1.3 | 3.65 | N.D | .12 | N.D | N.D | 74 |
| 4 | .625 | " | .86 | 4.2 | .04 | .18 | .39 | N.D | 82 |
| 5 | .75 | " | 1.1 | 4.7 | .11 | .22 | .50 | .03 | 82 |
| 6 | .875 | " | 1.2 | 3.9 | .04 | .16 | .39 | N.D | 78 |
| 7 | 1.0 | " | 1.8 | 3.4 | N.D | .15 | .19 | N.D | 88 |
| 8 | 2.0 | " | .47 | .45 | N.D | N.D | N.D | N.D | 46 |
| 9 | .125 | γ-butyrolactone | .9 | 1.9 | —[6] | — | — | — | 94 |
| 10 | .25 | " | 1.6 | 3.6 | — | — | — | — | 86 |
| 11 | .375 | " | 3.2 | 4.4 | — | — | — | — | 89 |
| 12 | .50 | " | 3.3 | 4.5 | — | — | — | — | 86 |
| 13 | .625 | " | 3.5 | 4.5 | — | — | — | — | 92 |
| 14 | .75 | " | 3.2 | 4.1 | — | — | — | — | 89 |

[1]All runs, 220°C., 8000 psia, $H_2/CO=1:1$, 3.0 mmol. Rhodium dicarbonyl Acetylacetonate and 10 mmol 2-hydroxypyridine ligand.
[2]bis(triphenylphosphine):minimum acetate containing about 1 mole of ethanol per mole of $(PH_3P)_2N^+$. Crystallized from Ethanol.
[3]Dimethyl ether of tetraethylene glycol.
[4]Measured the same as in example 1.
[5]Not detected on analysis.
[6]No minor product analysis was made in butyrolactone examples.

TABLE II[1]

| Example | Solvent | Temperature, °C. | Products, grams Ethylene Glycol | Methanol | Rhodium[3] Recovery |
|---|---|---|---|---|---|
| 15 | Tetraglyme | 220 | 3.65 | 1.3 | 74 |
| 16 | Tetraglyme | 240 | 5.3 | 2.9 | 61 |
| 17 | γ-butyrolactone | 220 | 2.3 | 1.75 | 94 |
| 18 | " | 230 | 3.6 | 2.5 | 98 |
| 19 | " | 240 | 4.5 | 3.3 | 86 |
| 20 | " | 250 | 5.3 | 3.7 | 83 |
| 21 | monoglyme[2] | 220 | .8 | .63 | 52 |
| 22 | ethanol | 220 | 2.2 | 1.1 | 60 |
| 23 | valerolactone | 240 | 4.3 | 2.9 | 86 |

[1]All runs at 8000 psig.; $H_2/CO = 1/1$; 75 cc solvent, 3.0 mmol. Rhodium dicarbonyl acetyl acetonate, 10 mmol 2-hydroxypyridine as ligand; 0.5 mmol. bis(triphenylphosphine) iminium acetate·1 ethanol solvate.
[2]dimethyl ether of ethylene glycol
[3]Measured the same as example 1.

TABLE III[1]

| Example | Counter-ion mmol. | $(Ph_3P)_2N^{+2}$ mmol | Ethylene Glycol | Methanol | Methyl Formate | Products, grams Glycol Monoformate | Glycerine | Rhodium Recovery |
|---|---|---|---|---|---|---|---|---|
| 24 | 4-methyl pyridine, 1.25 | .75 | 4.85 | 1.53 | .10 | .15 | .28 | 87 |
| 25 | piperidine, 1.25 | .75 | 4.7 | 1.42 | .08 | .14 | .34 | 78 |
| 26 | pyridine, 2.5 | .90 | 4.5 | 1.7 | .12 | .14 | .20 | 93 |
| 27 | pyridine, .625 | .90 | 3.1 | 1.2 | .09 | .10 | — | 82 |
| 28 | pyridine, 2.5 | .625 | 4.5 | 1.5 | .10 | .13 | .11 | 82 |
| 29 | pyridine, .625 | .625 | 5.25 | 1.37 | .08 | .17 | .23 | 91 |

[1]All runs at 8000 psig; $H_2/CO = 1:1$; 220°C.; 4 hours reaction time; 3.0 mmol rhodium dicarbonyl acetylacetonate; 75 milliliters dimethyl ether of tetraethylene glycol;
[2]bis(triphenylphosphine) iminium acetate·1 ethanol; crystallized from ethanol as ethanol solvate.

TABLE IV[1]

| Example | (Ph$_3$P)$_2$N$^+$[2] mmol | Rhodium mmol | Product, grams Ethylene Glycol | Methanol |
|---|---|---|---|---|
| 30 | 0.8 | 3.0 | 2.89 | 1.49 |
| 31 | 1.4 | 8.3 | 2.09 | 3.42 |
| 32 | 1.4 | 8.3 | 2.48 | 3.42 |
| 33 | 1.7 | 8.3 | 7.17 | 2.36 |
| 34 | 1.7 | 8.3 | 6.30 | 2.42 |
| 35 | 2.1 | 8.3 | 8.06 | 3.26 |

[1]All runs at 8000 psig; H$_2$/CO=1:1; 75 cc dimethyl ether of tetraethylene glycol as solvent; 220°C; 4 hours reaction time.
[2]bis(triphenyl phosphine)iminium acetate ·1 ethanol. Crystallized from ethanol as ethanol solvate (contains one mole of ethanol per mole of crystallized salt).

TABLE V[1]

| Example | (Ph$_3$P)$_2$N$^+$[2], mmol | Methanol | Product, grams Ethylene Glycol | Methyl Formate | Glycol Monoformate |
|---|---|---|---|---|---|
| 36 | .5 | 1.76 | 3.6 | 0.12 | 0.10 |
| 37 | .625 | 1.4 | 4.95 | 0.11 | 0.17 |
| 38 | .75 | 1.5 | 4.80 | 0.12 | 0.18 |
| 39 | .875 | 1.8 | 4.20 | 0.14 | 0.15 |

[1]All runs at 8000 psig; 220°C.; H$_2$/CO = 1/1; 75 cc. dimethyl ether of tetraethylene glycol as solvent; 3.0 mmol. of Rh$_4$(CO)$_{12}$; 1.25 mol of pyridine; 4 hours reaction time.
[2]bis(triphenyl phosphine)iminium acetate·1 ethanol. Crystallized from ethanol as ethanol solvate (contains one mole of ethanol per mole of crystallized salt).

What is claimed is:

1. A process for making alkane polyols which comprises reacting at a pressure of from about 500 psia to about 50,000 psia and a temperature of about 100°C. to about 375°C., a mixture consisting essentially of oxides of carbon and hydrogen in the presence of a bis(triorgano phosphine) iminium cation of the formula

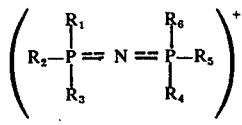

wherein R$_1$, R$_2$, R$_3$, R$_4$, R$_5$ and R$_6$ are alkyl, cycloalkyl, aryl, alkaryl, araalkyl, beta-hydroxyethyl, ethoxymethyl, ethoxylethyl, phenoxyethyl or a polyalkylene ether group of the formula C$_n$ H$_{2n}$ O)$_x$-OR wherein n has an average value from 1 to 4, x has an average value from 2 to about 150, and R may be hydrogen or alkyl of 1 to about 12 carbon atoms and a rhodium carbonyl complex, said complex is provided to the reaction as a rhodium carbonyl cluster which possesses an infrared spectrum which exhibits three intense wavelength bands between about plus and minus 10 cm$^{-1}$ of about 1868 cm$^{-1}$, about 1838 cm$^{-1}$, and about 1785 cm$^{-1}$, at a pressure of at least about 500 pounds per square inch absolute.

2. The process of claim 1 wherein the cation is present in about 0.8 to about 2.0 moles of cation for every six moles of rhodium.

3. The process of claim 2 wherein the cation is present in about 1.2 to about 1.6 moles of cation for every six moles of rhodium.

4. The process of claim 3 wherein the cation is present in about 1.2 to about 1.4 moles of cation for every six moles of rhodium.

5. The process of claim 1 wherein the cation is the bis(triphenyl phosphine) iminium cation.

6. The process of claim 1 wherein the reaction is effected in the presence of an inert solvent.

7. The process of claim 1 wherein the solvent is a dialkyl ether of alkylene glycols or polyalkylene glycol.

8. The process of claim 7 wherein the solvent is the dimethylether of tetraethylene glycol.

9. The process of claim 8 wherein the temperature of the reaction is from about 150°C. to about 300°C.

10. The process of claim 9 wherein the temperature of the reaction is from about 190°C. to about 275°C.

11. The process of claim 10 wherein the temperatures of the reaction is from about 190°C. to about 240°C.

12. The process of claim 1 wherein the reaction is conducted under a pressure ranging from about 1000 pounds per square inch absolute to about 15,000 pounds per square inch absolute.

13. The process of claim 12 wherein the reaction is conducted under a pressure ranging from about 2,000 pounds per square inch absolute to about 12,000 pounds per square inch absolute.

14. The process of claim 1 wherein at least one of an organic nitrogen ligand, an organic oxygen ligand, or an organic aza-oxa ligand is present in said rhodium carbonyl complex.

15. The process of claim 14 wherein the ligand is an organic aza-oxa ligand.

16. The process of claim 15 wherein the organic aza-oxa ligand is 2-hydroxypyridine.

17. The process of claim 1 wherein an organic nitrogen counter-ion containing a Lewis base nitrogen is present in said rhodium carbonyl complex.

18. The process of claim 17 wherein the organic nitrogen counter-ion is pyridine.

* * * * *